US010617297B2

(12) United States Patent
Turner

(10) Patent No.: US 10,617,297 B2
(45) Date of Patent: Apr. 14, 2020

(54) EARPIECE WITH IN-EAR ELECTRODES

(71) Applicant: BRAGI GmbH, München (DE)

(72) Inventor: Jake Berry Turner, München (DE)

(73) Assignee: BRAGI GmbH, München (DE)

( * ) Notice: Subject to any disclaimer, the term of this patent is extended or adjusted under 35 U.S.C. 154(b) by 273 days.

(21) Appl. No.: 15/796,370

(22) Filed: Oct. 27, 2017

(65) Prior Publication Data

US 2018/0116514 A1 May 3, 2018

Related U.S. Application Data

(60) Provisional application No. 62/416,537, filed on Nov. 2, 2016.

(51) Int. Cl.
*A61B 5/00* (2006.01)
*A61B 5/0478* (2006.01)
(Continued)

(52) U.S. Cl.
CPC .......... *A61B 5/0006* (2013.01); *A61B 5/0478* (2013.01); *A61B 5/6817* (2013.01); *A61B 5/7203* (2013.01); *G16H 40/63* (2018.01); *A61B 5/0031* (2013.01); *A61B 5/04004* (2013.01); *A61B 5/048* (2013.01); (Continued)

(58) Field of Classification Search
CPC ... A61B 5/0006; A61B 5/6878; A61B 5/0478; A61B 5/04012; A61B 5/0031; A61B 5/7203; A61B 5/0424; A61B 5/04004; A61B 5/0482; A61B 5/04845; A61B 5/048; A61B 5/6815; A61B 5/6801; A61B 5/6802; A61B 5/6803; A61B 5/6813; A61B 5/6817
See application file for complete search history.

(56) References Cited

U.S. PATENT DOCUMENTS 2,325,590 A 8/1943 Carlisle et al.
2,430,229 A 11/1947 Kelsey
(Continued)

FOREIGN PATENT DOCUMENTS

CN 204244472 U 4/2015
CN 104683519 A 6/2015
(Continued)

OTHER PUBLICATIONS

Akkermans, "Acoustic Ear Recognition for Person Identification", Automatic Identification Advanced Technologies, 2005 pp. 219-223.
(Continued)

*Primary Examiner* — Eric F Winakur
*Assistant Examiner* — Chu Chuan Liu
(74) *Attorney, Agent, or Firm* — Goodhue, Coleman & Owens, P.C.

(57) ABSTRACT

In some embodiments, an electronic device for monitoring EEG data, may include one or more of the following features: (a) a housing, (b) a processor disposed within the housing, (c) at least one sensor operatively connected to the processor, (d) at least two EEG electrodes operatively connected to the processor and positioned on the housing for receiving EEG signals from an ear surface, and (e) a plurality of EEG electrodes, wherein the processor measures the impedance of the plurality of EEG electrodes.

12 Claims, 7 Drawing Sheets

(51) Int. Cl.
*G16H 40/63* (2018.01)
*A61B 5/04* (2006.01)
*A61B 5/0482* (2006.01)
*G06F 19/00* (2018.01)
*A61B 5/0484* (2006.01)
*A61B 5/048* (2006.01)
*A61B 5/0424* (2006.01)

(52) U.S. Cl.
CPC ......... *A61B 5/04012* (2013.01); *A61B 5/0424* (2013.01); *A61B 5/0482* (2013.01); *A61B 5/04845* (2013.01); *G06F 19/3418* (2013.01)

(56) References Cited

U.S. PATENT DOCUMENTS

| | | | |
|---|---|---|---|
| 3,047,089 A | 7/1962 | Zwislocki |
| D208,784 S | 10/1967 | Sanzone |
| 3,586,794 A | 6/1971 | Michaelis |
| 3,934,100 A | 1/1976 | Harada |
| 3,983,336 A | 9/1976 | Malek et al. |
| 4,069,400 A | 1/1978 | Johanson et al. |
| 4,150,262 A | 4/1979 | Ono |
| 4,334,315 A | 6/1982 | Ono et al. |
| D266,271 S | 9/1982 | Johanson et al. |
| 4,375,016 A | 2/1983 | Harada |
| 4,577,639 A * | 3/1986 | Simon .................. A61B 5/0424 600/509 |
| 4,588,867 A | 5/1986 | Konomi |
| 4,617,429 A | 10/1986 | Bellafiore |
| 4,654,883 A | 3/1987 | Iwata |
| 4,682,180 A | 7/1987 | Gans |
| 4,791,673 A | 12/1988 | Schreiber |
| 4,852,177 A | 7/1989 | Ambrose |
| 4,865,044 A | 9/1989 | Wallace et al. |
| 4,984,277 A | 1/1991 | Bisgaard et al. |
| 5,008,943 A | 4/1991 | Arndt et al. |
| 5,185,802 A | 2/1993 | Stanton |
| 5,191,602 A | 3/1993 | Regen et al. |
| 5,201,007 A | 4/1993 | Ward et al. |
| 5,201,008 A | 4/1993 | Arndt et al. |
| D340,286 S | 10/1993 | Seo |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,347,584 A | 9/1994 | Narisawa |
| 5,363,444 A | 11/1994 | Norris |
| D367,113 S | 2/1996 | Weeks |
| 5,497,339 A | 3/1996 | Bernard |
| 5,606,621 A | 2/1997 | Reiter et al. |
| 5,613,222 A | 3/1997 | Guenther |
| 5,654,530 A | 8/1997 | Sauer et al. |
| 5,692,059 A | 11/1997 | Kruger |
| 5,721,783 A | 2/1998 | Anderson |
| 5,748,743 A | 5/1998 | Weeks |
| 5,749,072 A | 5/1998 | Mazurkiewicz et al. |
| 5,771,438 A | 6/1998 | Palermo et al. |
| D397,796 S | 9/1998 | Yabe et al. |
| 5,802,167 A | 9/1998 | Hong |
| D410,008 S | 5/1999 | Almqvist |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,084,526 A | 7/2000 | Blotky et al. |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| D455,835 S | 4/2002 | Anderson et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,690,807 B1 | 2/2004 | Meyer |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,010,137 B1 | 3/2006 | Leedom et al. |
| 7,113,611 B2 | 9/2006 | Leedom et al. |
| D532,520 S | 11/2006 | Kampmeier et al. |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| D549,222 S | 8/2007 | Huang |
| D554,756 S | 11/2007 | Sjursen et al. |
| 7,403,629 B1 | 7/2008 | Aceti et al. |
| D579,006 S | 10/2008 | Kim et al. |
| 7,463,902 B2 | 12/2008 | Boesen |
| 7,508,411 B2 | 3/2009 | Boesen |
| D601,134 S | 9/2009 | Elabidi et al. |
| 7,825,626 B2 | 11/2010 | Kozisek |
| 7,965,855 B1 | 6/2011 | Ham |
| 7,979,035 B2 | 7/2011 | Griffin et al. |
| 7,983,628 B2 | 7/2011 | Boesen |
| D647,491 S | 10/2011 | Chen et al. |
| 8,095,188 B2 | 1/2012 | Shi |
| 8,108,143 B1 | 1/2012 | Tester |
| 8,140,357 B1 | 3/2012 | Boesen |
| D666,581 S | 9/2012 | Perez |
| 8,300,864 B2 | 10/2012 | Müllenborn et al. |
| 8,406,448 B2 | 3/2013 | Lin |
| 8,436,780 B2 | 5/2013 | Schantz et al. |
| D687,021 S | 7/2013 | Yuen |
| 8,719,877 B2 | 5/2014 | VonDoenhoff et al. |
| 8,774,434 B2 | 7/2014 | Zhao et al. |
| 8,831,266 B1 | 9/2014 | Huang |
| 8,891,800 B1 | 11/2014 | Shaffer |
| 8,994,498 B2 | 3/2015 | Agrafioti et al. |
| D728,107 S | 4/2015 | Martin et al. |
| 9,013,145 B2 | 4/2015 | Castillo et al. |
| 9,037,125 B1 | 5/2015 | Kadous |
| D733,103 S | 6/2015 | Jeong et al. |
| 9,081,944 B2 | 7/2015 | Camacho et al. |
| 9,510,159 B1 | 11/2016 | Cuddihy et al. |
| D773,439 S | 12/2016 | Walker |
| D775,158 S | 12/2016 | Dong et al. |
| D777,710 S | 1/2017 | Palmborg et al. |
| 9,544,689 B2 | 1/2017 | Fisher et al. |
| D788,079 S | 5/2017 | Son et al. |
| 2001/0005197 A1 | 6/2001 | Mishra et al. |
| 2001/0027121 A1 | 10/2001 | Boesen |
| 2001/0043707 A1 | 11/2001 | Leedom |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |

(56) References Cited

U.S. PATENT DOCUMENTS

| | | |
|---|---|---|
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0094839 A1 | 5/2005 | Gwee |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |
| 2006/0029246 A1 | 2/2006 | Boesen |
| 2006/0073787 A1 | 4/2006 | Lair et al. |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0258412 A1 | 11/2006 | Liu |
| 2007/0135727 A1* | 6/2007 | Virtanen ............ A61B 5/04004 600/544 |
| 2008/0076972 A1 | 3/2008 | Dorogusker et al. |
| 2008/0090622 A1 | 4/2008 | Kim et al. |
| 2008/0146890 A1 | 6/2008 | LeBoeuf et al. |
| 2008/0187163 A1 | 8/2008 | Goldstein et al. |
| 2008/0253583 A1 | 10/2008 | Goldstein et al. |
| 2008/0254780 A1 | 10/2008 | Kuhl et al. |
| 2008/0255430 A1 | 10/2008 | Alexandersson et al. |
| 2009/0003620 A1 | 1/2009 | McKillop et al. |
| 2009/0008275 A1 | 1/2009 | Ferrari et al. |
| 2009/0017881 A1 | 1/2009 | Madrigal |
| 2009/0073070 A1 | 3/2009 | Rofougaran |
| 2009/0097689 A1 | 4/2009 | Prest et al. |
| 2009/0105548 A1 | 4/2009 | Bart |
| 2009/0154739 A1 | 6/2009 | Zellner |
| 2009/0191920 A1 | 7/2009 | Regen et al. |
| 2009/0245559 A1 | 10/2009 | Boltyenkov et al. |
| 2009/0261114 A1 | 10/2009 | McGuire et al. |
| 2009/0296968 A1 | 12/2009 | Wu et al. |
| 2010/0033313 A1 | 2/2010 | Keady et al. |
| 2010/0203831 A1 | 8/2010 | Muth |
| 2010/0210212 A1 | 8/2010 | Sato |
| 2010/0217100 A1 | 8/2010 | LeBoeuf et al. |
| 2010/0320961 A1 | 12/2010 | Castillo et al. |
| 2011/0140844 A1 | 6/2011 | McGuire et al. |
| 2011/0239497 A1 | 10/2011 | McGuire et al. |
| 2011/0286615 A1 | 11/2011 | Olodort et al. |
| 2012/0057740 A1 | 3/2012 | Rosal |
| 2013/0316642 A1 | 11/2013 | Newham |
| 2013/0346168 A1 | 12/2013 | Zhou et al. |
| 2014/0079257 A1 | 3/2014 | Ruwe et al. |
| 2014/0106677 A1 | 4/2014 | Altman |
| 2014/0122116 A1 | 5/2014 | Smythe |
| 2014/0153768 A1 | 6/2014 | Hagen et al. |
| 2014/0163771 A1 | 6/2014 | Demeniuk |
| 2014/0185828 A1 | 7/2014 | Helbling |
| 2014/0219467 A1 | 8/2014 | Kurtz |
| 2014/0222462 A1 | 8/2014 | Shakil et al. |
| 2014/0235169 A1 | 8/2014 | Parkinson et al. |
| 2014/0270227 A1 | 9/2014 | Swanson |
| 2014/0270271 A1 | 9/2014 | Dehe et al. |
| 2014/0335908 A1 | 11/2014 | Krisch et al. |
| 2014/0348367 A1 | 11/2014 | Vavrus et al. |
| 2015/0028996 A1 | 1/2015 | Agrafioti et al. |
| 2015/0035643 A1 | 2/2015 | Kursun |
| 2015/0036835 A1 | 2/2015 | Chen |
| 2015/0110587 A1 | 4/2015 | Hori |
| 2015/0148989 A1 | 5/2015 | Cooper et al. |
| 2015/0245127 A1 | 8/2015 | Shaffer |
| 2015/0373467 A1 | 12/2015 | Gelter |
| 2015/0373474 A1 | 12/2015 | Kraft et al. |
| 2016/0033280 A1 | 2/2016 | Moore et al. |
| 2016/0072558 A1 | 3/2016 | Hirsch et al. |
| 2016/0073189 A1 | 3/2016 | Linden et al. |
| 2016/0125892 A1 | 5/2016 | Bowen et al. |
| 2016/0353196 A1 | 12/2016 | Baker et al. |
| 2016/0360350 A1 | 12/2016 | Watson et al. |
| 2017/0059152 A1 | 3/2017 | Hirsch et al. |
| 2017/0060262 A1 | 3/2017 | Hviid et al. |
| 2017/0060269 A1 | 3/2017 | Forstner et al. |
| 2017/0061751 A1 | 3/2017 | Loermann et al. |
| 2017/0062913 A1 | 3/2017 | Hirsch et al. |
| 2017/0064426 A1 | 3/2017 | Hviid |
| 2017/0064428 A1 | 3/2017 | Hirsch |
| 2017/0064432 A1 | 3/2017 | Hviid et al. |
| 2017/0064437 A1 | 3/2017 | Hviid et al. |
| 2017/0078780 A1 | 3/2017 | Qian et al. |
| 2017/0078785 A1 | 3/2017 | Qian et al. |
| 2017/0108918 A1 | 4/2017 | Boesen |
| 2017/0109131 A1 | 4/2017 | Boesen |
| 2017/0110124 A1 | 4/2017 | Boesen et al. |
| 2017/0110899 A1 | 4/2017 | Boesen |
| 2017/0111723 A1 | 4/2017 | Boesen |
| 2017/0111725 A1 | 4/2017 | Boesen et al. |
| 2017/0111726 A1 | 4/2017 | Martin et al. |
| 2017/0111740 A1 | 4/2017 | Hviid et al. |
| 2017/0127168 A1 | 5/2017 | Briggs et al. |
| 2017/0142511 A1 | 5/2017 | Dennis |
| 2017/0151447 A1 | 6/2017 | Boesen |
| 2017/0151668 A1 | 6/2017 | Boesen |
| 2017/0151918 A1 | 6/2017 | Boesen |
| 2017/0151930 A1 | 6/2017 | Boesen |
| 2017/0151957 A1 | 6/2017 | Boesen |
| 2017/0151959 A1 | 6/2017 | Boesen |
| 2017/0153114 A1 | 6/2017 | Boesen |
| 2017/0153636 A1 | 6/2017 | Boesen |
| 2017/0154532 A1 | 6/2017 | Boesen |
| 2017/0155985 A1 | 6/2017 | Boesen |
| 2017/0155992 A1 | 6/2017 | Perianu et al. |
| 2017/0155993 A1 | 6/2017 | Boesen |
| 2017/0155997 A1 | 6/2017 | Boesen |
| 2017/0155998 A1 | 6/2017 | Boesen |
| 2017/0156000 A1 | 6/2017 | Boesen |
| 2017/0178631 A1 | 6/2017 | Boesen |
| 2017/0180842 A1 | 6/2017 | Boesen |
| 2017/0180843 A1 | 6/2017 | Perianu et al. |
| 2017/0180897 A1 | 6/2017 | Perianu |
| 2017/0188127 A1 | 6/2017 | Perianu et al. |
| 2017/0188132 A1 | 6/2017 | Hirsch et al. |
| 2017/0193978 A1 | 7/2017 | Goldman |
| 2017/0195829 A1 | 7/2017 | Belverato et al. |
| 2017/0208393 A1 | 7/2017 | Boesen |
| 2017/0214987 A1 | 7/2017 | Boesen |
| 2017/0215016 A1 | 7/2017 | Dohmen et al. |
| 2017/0230752 A1 | 8/2017 | Dohmen et al. |
| 2017/0251933 A1 | 9/2017 | Braun et al. |
| 2017/0257698 A1 | 9/2017 | Boesen et al. |
| 2017/0263236 A1 | 9/2017 | Boesen et al. |
| 2017/0273622 A1 | 9/2017 | Boesen |

FOREIGN PATENT DOCUMENTS

| | | |
|---|---|---|
| CN | 104837094 A | 8/2015 |
| EP | 1469659 A1 | 10/2004 |
| EP | 1017252 A3 | 5/2006 |
| EP | 2903186 A1 | 8/2015 |
| GB | 2074817 | 4/1981 |
| GB | 2508226 A | 5/2014 |
| WO | 2008103925 A1 | 8/2008 |
| WO | 2007034371 A3 | 11/2008 |
| WO | 2011001433 A2 | 1/2011 |
| WO | 2012071127 A1 | 5/2012 |

(56) References Cited

FOREIGN PATENT DOCUMENTS

| WO | 2013134956 A1 | 9/2013 |
| WO | 2014046602 A1 | 3/2014 |
| WO | 2014043179 A3 | 7/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |

OTHER PUBLICATIONS

Announcing the $3,333,333 Stretch Goal (Feb. 24, 2014).
Ben Coxworth: "Graphene-based ink could enable low-cost, foldable electronics", "Journal of Physical Chemistry Letters", Northwestern University, (May 22, 2013).
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected—The personalized digital assistant", "http://bmwblog.com/2016/01/05/bmw-introduces-bmw-connected-the-personalized-digital-assistant", (Jan. 5, 2016).
BRAGI Is on Facebook (2014).
BRAGI Update—Arrival of Prototype Chassis Parts—More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Lets Get Ready to Rumble, A Lot to Be Done Over Christmas (Dec. 22, 2014).
BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From the First Month of Kickstarter—Update on Progress (Aug. 1, 2014).
BRAGI Update—Memories From the Second Month of Kickstarter—Update on Progress (Aug. 22, 2014).
BRAGI Update—New People @BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing-Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, on Track(May 16, 2015).
BRAGI Update—Beta2 Production and Factory Line(Aug. 20, 2015).
BRAGI Update—Certifications, Production, Ramping Up.
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2015).
BRAGI Update—On Track, Design Verification, How It Works and What's Next(Jul. 15, 2015).
BRAGI Update—On Track, on Track and Gems Overview.
BRAGI Update—Status on Wireless, Supply, Timeline and Open House@BRAGI(Apr. 1, 2015).
BRAGI Update—Unpacking Video, Reviews on Audio Perform and Boy Are We Getting Close(Sep. 10, 2015).
Healthcare Risk Management Review, "Nuance updates computer-assisted physician documentation solution" (Oct. 20, 2016).
Hoffman, "How to Use Android Beam to Wirelessly Transfer Content Between Devices", (Feb. 22, 2013).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces a Health + Mobility Concept for Wellness in Mobility", Fountain Valley, Californa (2017).
International Search Report & Written Opinion, PCT/EP2016/070231 (dated Nov. 18, 2016).
Last Push Before the Kickstarter Campaign Ends on Monday 4pm CET (Mar. 28, 2014).
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).
Nuance, "ING Netherlands Launches Voice Biometrics Payment System in the Mobile Banking App Powered by Nuance", "https://www.nuance.com/about-us/newsroom/press-releases/ing-netherlands-launches-nuance-voice-biometrics.html", 4 pages (Jul. 28, 2015).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for the Dash (Feb. 12, 2014).
Stretchgoal—Windows Phone Support (Feb. 17, 2014).
The Dash + The Charging Case & The BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).
Wertzner et al., "Analysis of fundamental frequency, jitter, shimmer and vocal intensity in children with phonological disorders", V. 71, n.5, 582-588, Sep./Oct. 2005; Brazilian Journal of Othrhinolaryngology.
Wikipedia, "Gamebook", https://en.wikipedia.org/wiki/Gamebook, Sep. 3, 2017, 5 pages.
Wikipedia, "Kinect", "https://en.wikipedia.org/wiki/Kinect", 18 pages, (Sep. 9, 2017).
Wikipedia, "Wii Balance Board", "https://en.wikipedia.org/wiki/Wii_Balance_Board", 3 pages, (Jul. 20, 2017).

* cited by examiner

EARPIECE WITH IN-EAR ELECTRODES

PRIORITY STATEMENT

This application claims priority to U.S. Provisional Patent Application No. 62/416,537 titled Earpiece with In-Ear Electrodes, filed Nov. 2, 2016, hereby incorporated by reference in its entirety.

FIELD OF THE INVENTION

The present invention relates to wearable devices. Particularly, the present invention relates to wireless earpieces. More particularly, but not exclusively, the present invention relates to wireless earpieces having electrodes.

BACKGROUND

There is growing market demand for personal health monitors, for example, for gauging overall health and metabolism of persons during exercise, athletic training, dieting, and physical therapy. Various physiological information, such as electrocardiogram (ECG) information, electroencephalogram (EEG) information, electrooculography (EOG) information, and other forms of physiological electrical activity, may be useful to monitor during physical activity. However, traditional monitors for measuring this type of information may be bulky, rigid, non-portable, and uncomfortable—generally not suitable for use during physical activity.

Current methods of receiving EEG signals are very cumbersome and indiscreet. In order to get an accurate reading of a user's brain waves, a medical professional or a person trained in electrode placement must place electrodes at certain spots on a user's head in order to obtain a usable reading. Problems with this method include the need for trained personnel to accurately place an electrode, attenuation of the EEG signals due to the skull, and possible infection from the electrode placement. Current research suggests, however, EEG signals may be received using an earpiece with electrodes attached at certain points make contact with an ear surface of the user. Using this method trained personnel are no longer needed and the EEG signal is less attenuated due to electrode placement within the ear canal. However, since the electrodes are so close together, it is difficult to get a good signal due to reduced spatial resolution and high impedances between the EEG electrodes and the skin.

Therefore, what is needed is a system and method of obtaining a usable EEG signal from a user using an earpiece.

SUMMARY

Therefore, it is a primary object, feature, or advantage of the present invention to improve over the state of the art.

In some embodiments, an electronic device for monitoring EEG data, may include one or more of the following features: (a) a housing, (b) a processor disposed within the housing, (c) at least one sensor operatively connected to the processor, (d) at least two EEG electrodes operatively connected to the processor and positioned on the housing for receiving EEG signals from an ear surface, and (e) a plurality of EEG electrodes, wherein the processor measures the impedance of the plurality of EEG electrodes.

In some embodiments a method of receiving an EEG signal from an ear surface may include one or more of the following steps: (a) transmitting a current to a plurality of EEG electrodes, (b) receiving at least one sensor reading from a sensor operatively connected to the processor, (c) communicating, a voltage drop associated with of the plurality of EEG electrodes to the processor, (d) determining an impedance of each of the plurality of EEG electrodes, (e) determining which of the impedances are below a programmed threshold for each of the plurality of EEG electrodes, (f) transmitting an activation signal to the plurality of EEG electrodes which have an impedance below the programmed threshold, (g) receiving an EEG signal from the plurality of EEG electrodes which have an impedance below the programmed threshold, (h) determining which of the plurality of electrodes do not have a reliable EEG signal based upon the at least one sensor reading, (i) receiving a sensor reading from a plurality of sensors, and (j) providing a reliable EEG signal based upon the EEG signal taken from the plurality of EEG electrodes which have an impedance below the programmed threshold and have the reliable EEG signal based upon the at least one sensor reading.

In some embodiments a system may include one or more of the following features: (a) a first earpiece having a housing, (b) a processor disposed within the housing, (c) at least one sensor disposed within the housing and operatively connected to the processor, wherein the at least one sensor is configured to sense user data and communicate the user data to the processor, and (d) a plurality of EEG electrodes operatively connected to the processor and positioned on the housing for receiving EEG signals from an ear surface, wherein the processor transmits a current to each of the plurality of EEG electrodes to determine an impedance from each of the plurality of EEG electrodes and subsequently communicates an activation signal to selected EEG electrodes if the impedance associated with the EEG electrode is below a programmed threshold.

One or more of these and/or other objects, features, or advantages of the present invention will become apparent from the specification and claims follow. No single embodiment need provide each and every object, feature, or advantage. Different embodiments may have different objects, features, or advantages. Therefore, the present invention is not to be limited to or by an objects, features, or advantages stated herein.

BRIEF DESCRIPTION OF THE DRAWINGS

Illustrated embodiments of the disclosure are described in detail below with reference to the attached drawing figures, which are incorporated by reference herein.

DETAILED DESCRIPTION

Figure 1:
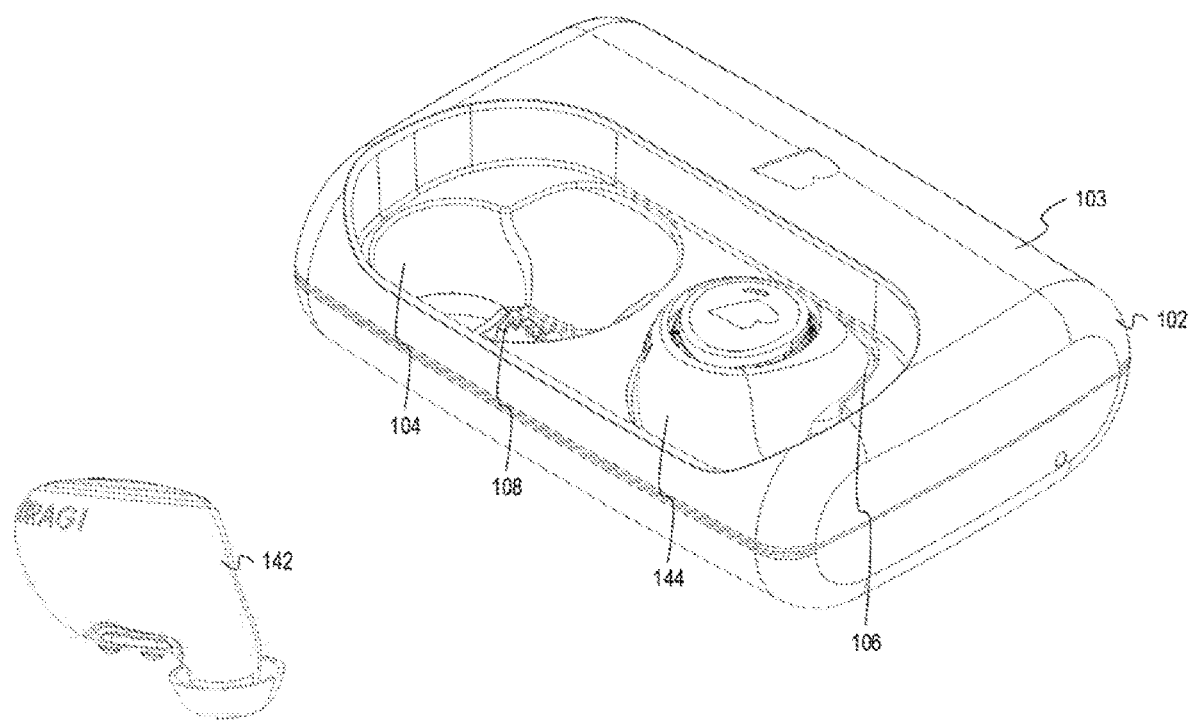
FIG. 1 is a pictorial representation of a smart case and wireless earpieces in accordance with an illustrative embodiment.

The following discussion is presented to enable a person skilled in the art to make and use the present teachings. Various modifications to the illustrated embodiments will be readily apparent to those skilled in the art, and the generic principles herein may be applied to other embodiments and applications without departing from the present teachings. Thus, the present teachings are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings. While embodiments of the present invention are discussed in terms of wearable devices and obtaining a useful signal from an onboard electrode, it is fully contemplated embodiments of the present invention could be used in most any electronic communications device without departing from the spirit of the invention.

While the present invention will be discussed, shown and illustrated as embodiments for a smart case and wireless earpieces, the inventor(s) fully contemplate embodiments of the present invention can be extended to all electronics and particularly to all mobile electronic devices and more particularly to all mobile electronic devices having or needing a connection to another electronic device in order to charge and/or communicate data. Examples of these devices include mobile phones, fitness monitoring devices, such as watches, eyewear, belts, etc. and implantable devices. Embodiments of the present invention can also be extended to electronic medical device applications as well including any devices which monitor and/or record physiological data and then download or report this data to a host device. The present invention could also be extended to other form of earpieces such as custom mold earpieces and/or visoelastic earplugs or earpieces. The inventor(s) further acknowledge there are many more electronic devices the present invention could be applied towards, which have not been named in the paragraph above. Therefore, the illustrative embodiments listed below in no way should be interpreted to limit the scope of embodiments of the present invention.

Embodiments of the present invention, discussed in great detail below, show many aspects of the current invention. An embodiment of the present invention details determining ideal locations and/or specific electrode(s) from which to receive an EEG signal. Another embodiment of the present invention details, being able to continuously determine ideal locations and or specific electrode(s) to receive an EEG signal. Another embodiment of the present invention details using sensor readings to ascertain ideal locations and/or electrode(s) to receive an EEG signal. Another embodiment of the present invention details using a differential amplifier in order to reduce common mode noise (when transmitting data, wires can act as antennas pick up a signal "noise" and this is undesirable). Another embodiment of the present invention details modifying one or more functions of a wireless earpiece based upon interpreted brain wave input.

In another embodiment, a wireless earpiece has a housing, a processor disposed within the housing, one or more sensor(s) operatively connected to the housing and the processor, and one or more EEG electrode(s) operatively connected to the processor and positioned on the housing for receiving EEG signals from an ear surface. Two or more of the EEG electrode(s) are positioned to contact an outer surface of an ear and to contact an inner surface of an ear canal.

One or more of the following features may be included in embodiments of the present invention. One or more of the sensor(s) may comprise an MEMS gyroscope (vibrating structure microelectromechanical systems), an electronic magnetometer (an instrument measuring magnetism—either the magnetization of a magnetic material like a ferromagnet, or the direction, strength, or relative change of a magnetic field at a particular location), or an electronic accelerometer (a device measuring acceleration). A differential amplifier (a device which amplifies the difference between two or more signals) may be disposed within the housing and operatively connected to each EEG electrode and the processor. The differential amplifier may further comprise at least one analog filter. An analog-to-digital converter may be disposed within the housing and operatively connected to the processor and the differential amplifier.

In another embodiment, a method of receiving an EEG signal from an ear surface using an earpiece is discussed in great detail below. The method includes transmitting, via a processor, a current to each EEG electrode and the processor receiving one or more sensor readings from a sensor operatively connected to the earpiece. Based upon this received sensor data, certain EEG electrodes may not be used to obtain data based upon a certain activity the user is performing which may make certain EEG electrodes unreliable or the data from them faulty. A voltage drop occurs at each EEG electrode based upon the current sent to the EEG electrode by the processor, and the processor obtains and records this voltage drop. From this voltage drop, the processor can calculate an impedance of each EEG electrode and determine which impedances are below a programmed threshold. The programmed threshold being an impedance below a certain level in which reliable data can be obtained from the EEG electrode. The processor sends an activation signal to the EEG electrodes based upon both the sensor readings and the impedances for each EEG electrode. The processor then receiving back a reliable EEG signal One or more of the following features may be included in embodiments of the present invention. One or more EEG electrodes may be positioned on a surface within an ear canal. Specifically, the EEG electrodes may be positioned on a concha, fossa, antihelix, antihelical fold or the scapha. The EEG signal may be further amplified by a differential amplifier to create an amplified EEG signal. The amplified EEG signal may be further filtered by the differential amplifier to create a filter amplified EEG signal. The filter amplified EEG signal may be sampled with an analog-to-digital converter to create a sampled filtered amplified EEG signal. The sampled filtered amplified EEG signal may be used to modify one or more functions of the earpiece.

One or more of the following features may be included to the embodiments listed below. User data may comprise motion data, which would be detected by sensors. The differential amplifier amplifies the difference between the voltages of two separate EEG signals to reduce common mode noise in the two separate EEG signals to create an amplified EEG signal. The differential amplifier may have a high pass filter and a low pass filter. An analog-to-digital converter may be disposed within the housing operatively connected to the processor and the differential amplifier, and the analog-to-digital converter samples the amplified EEG signal and communicates a sampled amplified EEG signal to the processor. The amplified EEG signal may be sampled at a rate at the Nyquist rate.

Figure 2:
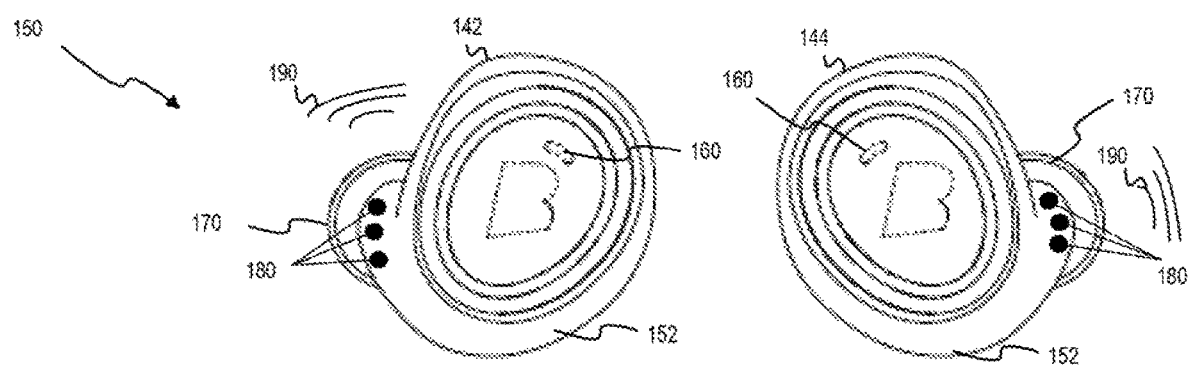
FIG. 2 is a pictorial representation of wireless earpieces having electrodes in accordance with an illustrative embodiment.

With reference to FIGS. 1 & 2, these figures show a pictorial representation of a smart case 102 and wireless earpieces 142, 144 in accordance with an illustrative embodiment. Throughout the invention disclosure reference will be sometimes made to only one of wireless earpieces 142, 144; however, it is to be understood any discussion of one wireless earpiece 142 can be applied to the other wireless earpiece 144 unless clearly pointed out in an embodiment of the present invention. The smart case 102 may be an open or enclosed case for securing, charging and managing the wireless earpieces 142, 144. The wireless earpieces 142, 144 may be referred to as a pair (wireless earpieces) or singularly (wireless earpiece). The description may also refer to components and functionality of each of the wireless earpieces 142, 144 collectively or individually. In one embodiment, the wireless earpieces 142, 144 include a set of left and right ear pieces configured to fit into a user's ears. The wireless earpieces 142, 144 may be configured to play music or audio, receive and make phone calls or other communications, determine ambient environmental readings (e.g., temperature, altitude, location, speed, heading, etc.), read user biometrics and actions (e.g., heart rate, motion, sleeping, etc.).

In another embodiment, the wireless earpieces 142, 144 may represent wireless devices, which may be ingested or implanted into a user. For example, the smart case 102 may be configured to work with endoscopic pills, pacemakers, tracking devices, contact lenses, oral implants, bone implants, artificial organs or so forth. The smart case 102 may act as a logging tool for receiving information, data, or measurements made by the wireless devices. For example, the smart case 102 may be attached to a belt (e.g., belt clip, strap, etc.) or worn by the user to download data from the wireless device(s) in real-time. As a result, the smart case 102 may be utilized to store, charge, and synchronize data for the wireless earpieces 142, 144 in any number of embodiments.

The smart case 102 encloses a battery, and various other circuitry. The battery of the smart case 102 may be utilized to charge the wireless earpieces 142, 144 through direct contact or wirelessly. As a result, the smart case 102 may act as a custom charger for ensuring the proper power management and functionality of the wireless earpieces 142, 144. For example, the battery of the smart case 102 may be utilized to charge the wireless earpieces 142, 144 any number of times before the smart case 102 and corresponding battery may require charging. In one embodiment, the smart case 102 may include one or more solar panels, or surfaces configured to charge the smart case 102 utilizing ambient or direct sunlight. The smart case 102 ensures the duty cycle of the wireless earpieces 142, 144 are maximized by properly maintaining power levels. For example, the smart case 102 may keep the wireless earpieces 142, 144 fully charged during a time period of inactivity, such as before being purchased (e.g., on a shelf or as part of inventory) or one purchased.

In one embodiment, the smart case 102 include a housing 103. The housing 103 is a support structure for the components of the smart case 102 and may be formed of a rigid plastic, polymer, or other similar material. However, any number of other suitable materials, such as composites, rubber, wood, metal, or so forth, may be utilized. The housing 103 defines receptacles 104, 106 are configured to receive the wireless earpieces 142, 144, respectively. In one embodiment, the receptacles 104, 106 are shaped to fit the external size, shape, and configuration of the wireless earpieces 142, 144.

As a result, an interface fit may secure the wireless earpieces 142, 144 within the housing 103 while the smart case 102 is being moved or otherwise utilized. In one embodiment, the smart case 102 may include a hinged, magnetic, sleeve, or snap on lid or cover may cover the wireless earpieces 142, 144 when positioned within the receptacles 104, 106 of the smart case 102. For example, the cover may make the smart case 102 waterproof and further secure the wireless earpieces 142, 144. In another embodiment, the smart case 102 may also include a removable cover (e.g., neoprene, zip up, snapping, etc.). In yet another embodiment, the cover encases a screen, such as a touch screen. The screen may roll, bend or adapt to the shape and configuration of the smart case 102. The touch screen may also be transparent. In one embodiment, the smart case 102 may be hermetically sealed and waterproof when the cover is secured. The smart case 102 may also include one or more speakers for playing music, indicating a status of the wireless earpieces 142, 144 or otherwise communicating information to the user. Likewise, actuators may be utilized to provide tactile feedback to the user. The case may have at least one button or other manual input. The button may be touch sensitive, lighted, or mechanical. There also may be a light such as a LED in location.

The smart case includes interfaces 108, 110 within the receptacles 104, 106. The interfaces 108, 110 are hardware interfaces for electrically connecting the wireless earpieces 142, 144 to the smart case 102. The interfaces 108, 110 may include any number of contact points, busses, wires, or other physical connectors for interfacing the wireless earpieces 142, 144, with the smart case 102. The interfaces 108, 110 may alternatively include inductive chargers for charging the wireless earpieces 142, 144. In another embodiment, the interfaces 108, 110 may represent male or alternatively female) connectors for interfacing with the wireless earpieces 142, 144, such as micro-USB, or other developing miniature external connectors. The interfaces 108, 110 may be utilized to charge the wireless earpieces 142, 144. The interfaces 108, 110 may also be utilized to synchronize data between the wireless earpieces 142, 144. As previously noted, wireless charging is also contemplated utilizing an inductive charger integrated in the smart case 102 or other charging devices compatible with the wireless earpieces 142, 144.

In another embodiment, the wireless earpieces 142, 144 and the smart case 102 may interact to control a device reset function. For example, the wireless earpieces 142, 144 may synchronize captured data with the smart case 102 before moving to a low power mode in anticipation of being charged. A switch may be activated mechanically, magnetically, inductively, electrically, or wirelessly in anticipation of being charged. For example, the smart case 102 may lower the power mode of the wireless earpieces 142, 144 in response to contacts of the wireless earpieces 142, 144 coming in contact with the interfaces 108, 110. For example, the smart case 102 may detect a change in resistance when the wireless earpieces 142, 144 are electrically connected to the interfaces 108, 110 to perform the processes herein described. In another embodiment, each of the interfaces 108, 110 may include a switch activated when one of the wireless earpieces 142, 144 is positioned within the receptacles. The interfaces 108, 110 may also include a pin when depressed or contacted by one of the wireless earpieces 142, 144 turns off the wireless earpieces 142, 144. Control of the wireless earpieces 142, 144 may be controlled by the smart case 102, the wireless earpieces 142, 144 themselves, or may be shared between devices.

In one embodiment, the interfaces, 108, 110 or another portion of the smart case 102 as well as the wireless earpieces 142, 144 may include a near field communication (NFC) chip for communications. For example, NFCs may determine the wireless earpieces 142, 144 are proximate the smart case 102 for performing power management. NFC may also be utilized to identify the wireless earpieces 142, 144 associated with a particular smart case 102. In other embodiments, different communications protocols (e.g., Bluetooth, Wi-Fi, etc.), standards, or passive readers radio frequency identification tags, etc.) may be utilized for the wireless earpieces 142, 144 to communicate with the smart case 102. For example, the smart case 102 may power off the wireless earpieces 142, 144 in response to being placed in or near the smart case 102. The smart case 102 may be programmed with a threshold distance (e.g., 10 cm, 1 foot, etc.) to determine when the wireless earpieces 142, 144 are proximate the smart case 102 or may rely on the inherent maximum communications distances of the wireless standard or protocol being utilized (e.g., NFC, RFID, etc.).

With reference to FIG. 2, a pair of earpieces 150 which includes a left earpiece 142 and a right earpiece 144. The wireless earpieces 142, 144 have a housing 152. The left earpiece 142 and the right earpiece 144 may be configured to substantially encompass an outer opening of a user's ear canal (see FIG. 3) and/or fit within the user's ear canal in order to maximize the amount of space available to place an EEG electrode 180. The housing 152 may be composed of metallic material, plastic material, or any material with substantial resistance to shear and tensile forces and may also be configured to be soundproof or waterproof. EEG electrodes 180 may be located anywhere on housing 152 conducive to obtaining a EEG signal from an ear surface and more EEG electrodes than the three shown on each earpiece may be found on housing 152. A microphone 160 is shown and may be located anywhere on the wireless earpieces 142, 144 and each microphone 160 may be configured to receive one or more voice commands. Speaker 170 may be configured to communicate audio sound 190. The audio sound 190 may be communicated to the user or a third party and speaker 170 may also be configured too short out if the sound intensity of the audio sound 190 is too high or otherwise surpasses a given threshold, which may be pre-programmed into a processor 414 (FIG. 4), a memory device 540 (FIG. 5), or set by the user or a third party.

Figure 3:
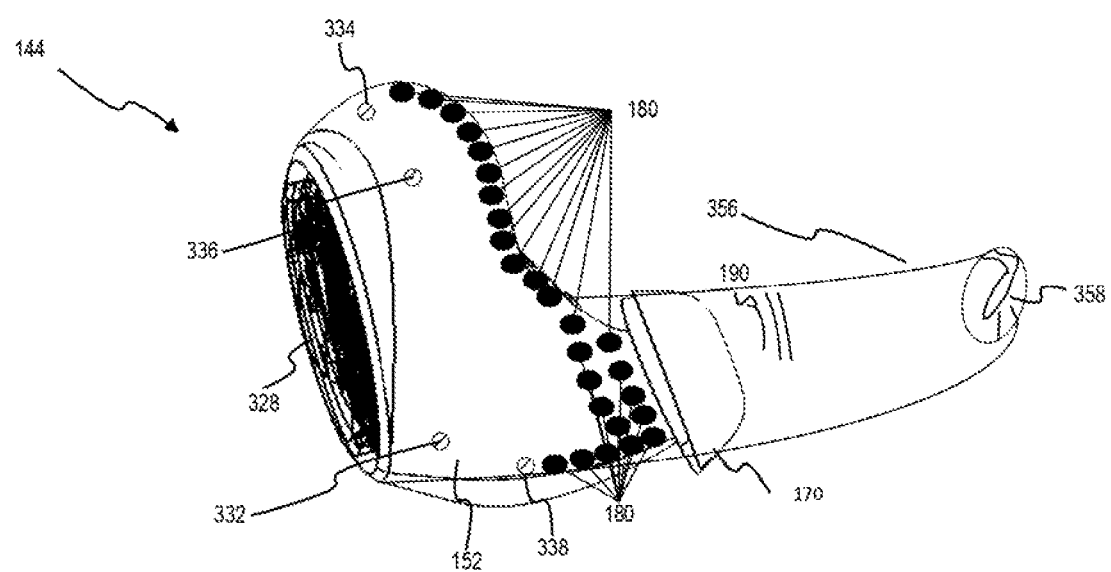
FIG. 3 is a pictorial representation of an earpiece with a plurality of EEG electrodes placed within a user's ear in accordance with an illustrative embodiment.

FIG. 3 illustrates a side view of the earpiece 144 and its relationship to a user's ear. The earpiece 144 may be configured to minimize the amount of external sound reaching the user's ear canal 356 and/or to facilitate the transmission of the audio sound 190 from the speaker 170 to a user's tympanic membrane 358. The earpiece 144 may also have a plurality of EEG electrodes 180 positioned throughout the outside of the earpiece 144. The EEG electrodes 180 may be of any size or shape capable of receiving an EEG signal and may be positioned anywhere along the housing 152 conducive to receiving an EEG signal. A gesture control interface 328 is shown on the exterior of the earpiece 144. The gesture control interface 328 may provide for gesture control by the user or a third party such as by tapping or swiping across the gesture control interface 328, tapping or swiping across another portion of the earpiece 144, providing a gesture not involving the touching of the gesture control interface 328 or another part of the earpiece 144, or through the use of an instrument configured to interact with the gesture control interface 328. A MEMS gyroscope 332, an electronic magnetometer 334, an electronic accelerometer 336 and a bone conduction microphone 338 are also shown on the exterior of the housing 152. The MEMS gyroscope 332 may be configured to sense rotational movement of the user's head and communicate the data to a processor, wherein the data may be used in removing any artifacts found in an EEG signal. The electronic magnetometer 334 may be configured to sense a direction the user is facing and communicate the data to the processor, which, like the MEMS gyroscope 332, may be used in removing artifacts from one or more EEG signals. The electronic accelerometer 336 may be configured to sense the force of the user's head when receiving EEG signals, which may be used by the processor in removing sound artifacts related to head movement. The bone conduction microphone 338 may be configured to receive body sounds from the user, which may be used by the processor or the differential amplifier 520 (FIG. 5) in filtering out unwanted sounds or noise from an EEG signal. The speaker 170 is also shown and may communicate the audio sound 190 in any manner conducive to facilitating the audio sound 190 to the user's tympanic membrane 358.

Figure 4:
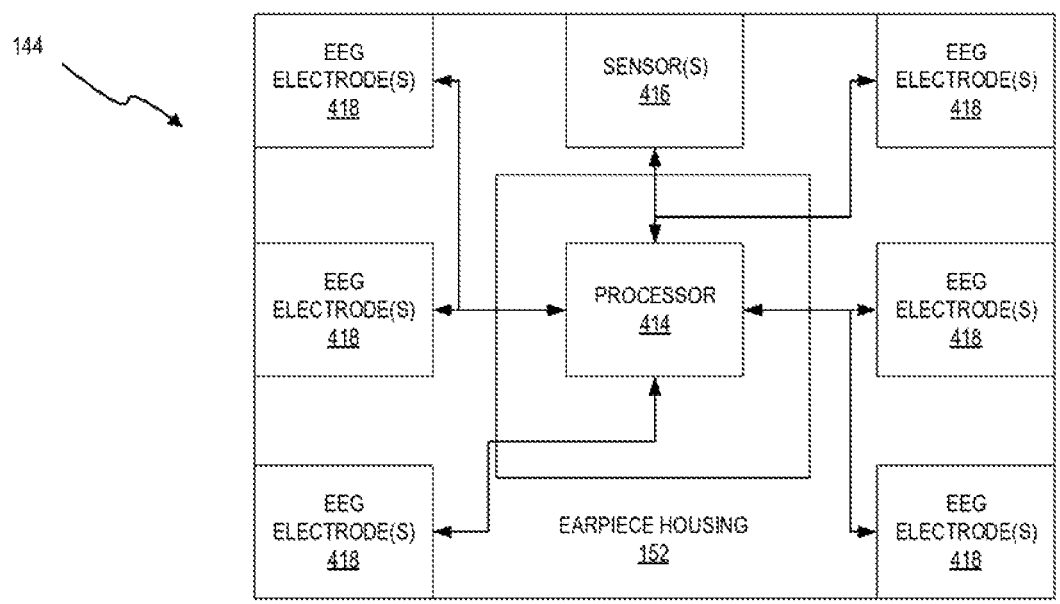
FIG. 4 is a block diagram of a wireless earpiece in accordance with an illustrative embodiment.

FIG. 4 shows a wireless earpiece 144 having an housing 152, a processor 414 disposed within the housing 152, at least one sensor 416 operatively connected to the earpiece housing 152 and the processor 414, and a plurality of EEG electrodes 418 operatively connected to the housing 152 and the processor 414, wherein at least one EEG electrode 418 is positioned to contact an outer surface of an ear canal and at least one EEG electrode 418 is positioned to contact an inner surface of an ear canal 356. The housing 152 may be made of any material suitable to hold each component of the earpiece 142, 144 together, which may include metallic, plastic, one or more polymers, or a combination thereof, and the housing 152 may be able to withstand a drop of more than three meters without breaking or having a component become loose or broken. The processor 414 may be positioned at any location within the housing 152 which is conducive to receiving or processing EEG signals and sensor readings and may have one or more additional electrical components operatively connected to processor 414 at any given time. One or more sensors 416 are operatively connected to the housing 152 and the processor 414 and positioned to sense user data from the user. One or more sensors 416 may comprise a MEMS gyroscope 332, an electric accelerometer 336, a bone conduction microphone 338, or any type of sensor conducive to helping the processor 414 read an EEG signal. As discussed briefly, the processor 414 can use the data from the sensors 416 in several ways. The processor 414 can receive data from the sensors 416, which would cause processor 414 to reject any input from certain electrodes 418 (i.e., certain movement or noise). The processor can also use the data from the sensors 416 to perform filtering of the electrode signal to eliminate any distortion or noise on the electrode signal, thus providing a better electrode signal. This decision process could be programmed into the processor based upon set limits or tolerances based on signals coming from each of the sensors or for the totality of the sensors.

For example, a MEMS gyroscope 332 may produce one or more currents due to one or more vibrating masses in response to a user head movement (which causes noise to appear on a EEG signal) in two or three axes via the Coriolis effect, which may be communicated to the processor 414 for determination of a head position. An electronic accelerometer 336 may produce a voltage in response to a user head movement (which causes noise to appear on a EEG signal) which causes a capacitance differential between two charged microstructures due to the user's head movement, which may be communicated to the processor 414 for determination of a head acceleration. Or a bone conduction microphone 338 may measure sounds from the body and communicate them to the processor 414, which may be used to improve the signal quality of one or more EEG signals.

A plurality of EEG electrodes 418 are operatively connected to the housing 152 and the processor 414, wherein at least one EEG electrode 418 is positioned to contact an outer surface of an ear surface and at least one EEG electrode 418 is positioned to contact an ear canal surface. The EEG electrodes 418 may have an outer surface composed of silver chloride to reduce the impedance between the electrode and the skin, and a conductive gel may be applied to the EEG electrodes 418 if necessary. An EEG electrode 418 positioned on either the outer or inner surface of the ear may act as a reference point to measure one or more EEG signals, and in some preferred embodiments a voltage of a single EEG signal is measured at two different electrodes relative to a reference electrode in order to improve signal quality by allowing a differential amplifier to remove any common mode gain present in both signals. An electronic filter may also be present to filter out any noise, usually in the 50-60 Hertz range, caused by consumer electrical appliances or gadgets or poor connections between the EEG electrodes 418 and one or more ear surfaces.

Figure 5:
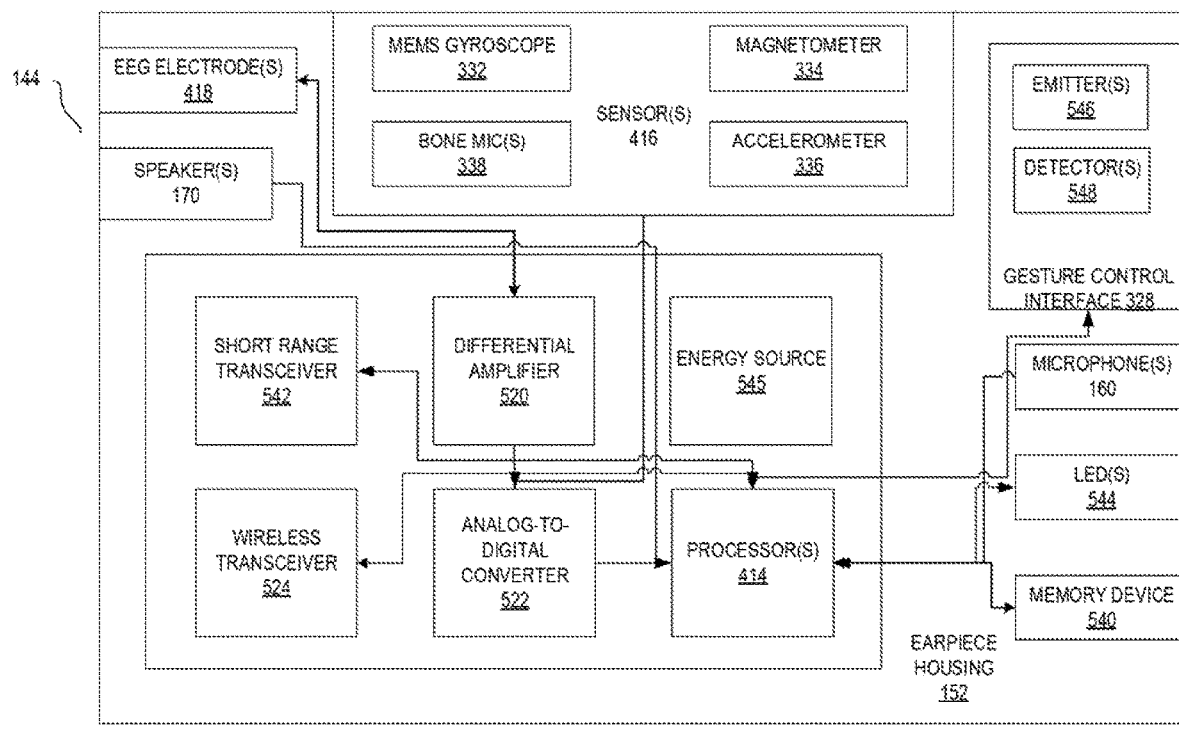
FIG. 5 is a block diagram of a wireless earpiece in accordance with an illustrative embodiment.
Figure 6:
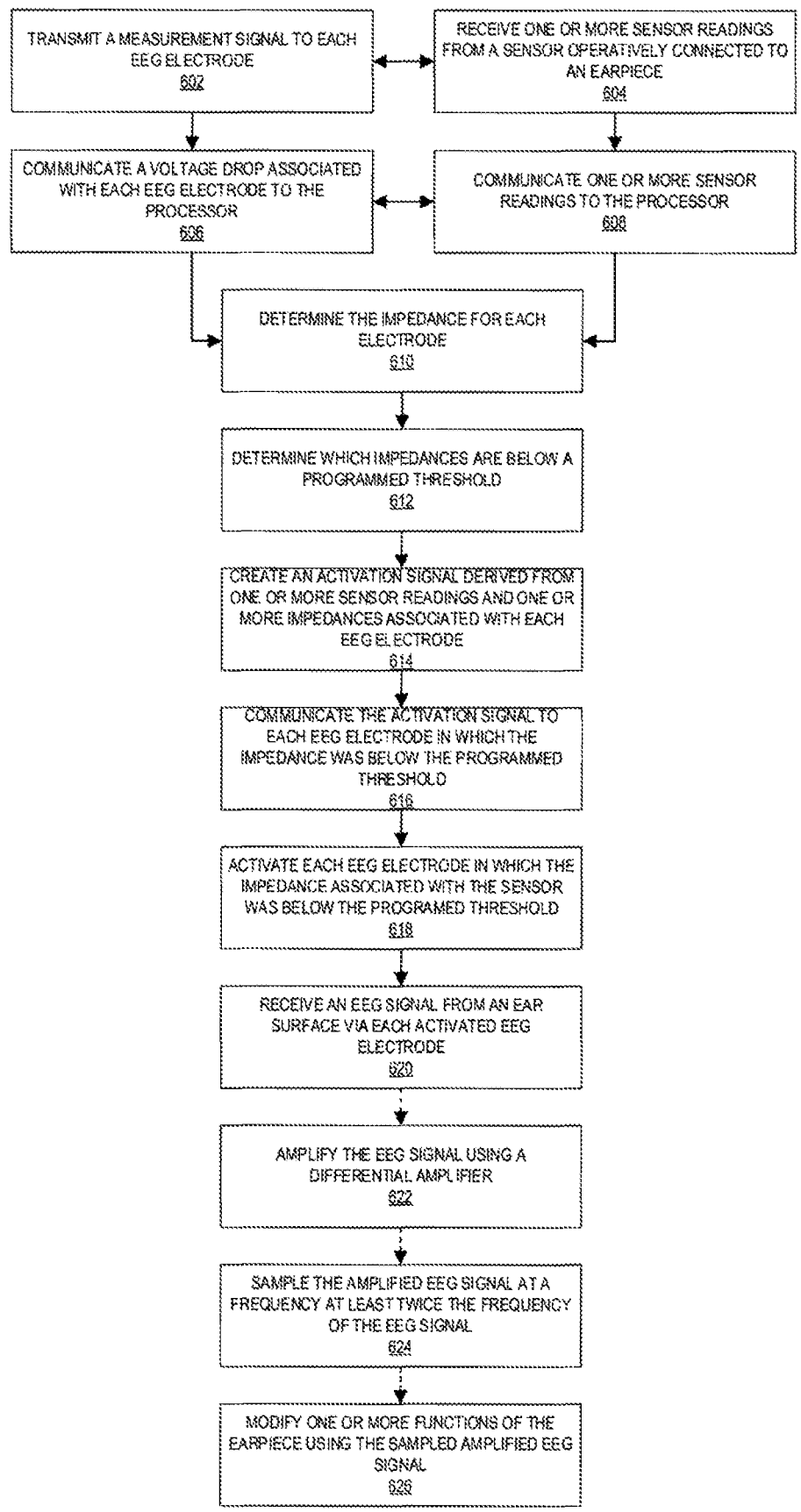
FIG. 6 is a block diagram for modifying a function of an earpiece using an EEG signal in accordance with an illustrative embodiment.

FIG. 5 is a block diagram of a system of an earpiece 144 comprising an housing 152, a processor 414 operatively connected to the housing 152, one or more sensors 416, which may comprise a MEMS gyroscope 332, an electronic magnetometer 334, an electric accelerometer 336 or a bone conduction microphone 338, operatively connected to the housing 152 and the processor 414, a plurality of EEG electrodes 418 operatively connected to the housing 152, a differential amplifier 520 operatively connected to the housing 152 and each EEG electrode 418, an analog-to-digital converter 522 operatively connected to the housing 152, processor 414, and differential amplifier 520, a wireless transceiver 524 operatively connected to the housing 152 and the processor 414, a microphone 160 operatively connected to the housing 152 and the processor 414, a gesture control interface 328 having an emitter 546 and a detector 548 operatively connected to the housing 152 and the processor 414, a speaker 170 operatively connected to the housing 152 and the processor 414, a memory device 540 operatively connected to the housing 152 and the processor 414, a short range transceiver 542 operatively connected to the housing 152 and the processor 414, and LEDs 544 operatively connected to the housing 152 and the processor 414.

The processor 414 is disposed within the housing 152 and operatively connected to one or more sensors 416, each EEG electrode 418, the analog-to-digital converter 522, the wireless transceiver 524, the gesture control interface 328, the speaker 160, the memory device 540, the transceiver 542, LEDs 544, and an energy source 545. The processor 414 may transmit a measurement signal of a known current to each EEG electrode in order to ascertain an impedance associated with each EEG electrode 418 via a voltage drop across each EEG electrode 418. The processor 414 may perform this continuously or intermittently at a synchronous or asynchronous rate, keeping in mind the measurement signal may interfere with any EEG signal measurements by an EEG electrode 418. Thus these measurement signals will need to be properly timed so as to not add to the problem the present invention aims to solve, namely bad or corrupted EEG data from electrodes 418. The processor 414 may receive digital signals from an EEG electrode 418, which have been sampled by an analog-to-digital converter 522 and amplified and filtered by the differential amplifier 520, in which the digital signals may be used to control the earpiece 144. For example, the EEG electrode 418 may measure changes in a user's mu waves (mu waves, also known as mu rhythms, comb or wicket rhythms, arciform rhythms, or sensorimotor rhythms, are synchronized patterns of electrical activity involving large numbers of neurons, and are most prominent when the body is physically at rest) during the performance of a certain action, such as tapping the tips of their right index finger and thumb together, which may be communicated to the processor 414 and used to turn the earpiece 144 on or off. The processor 414 may process the waves using, for example, a Fourier transform to decompose the EEG signal into its frequency components from an algorithm stored on the memory device 540 or within the processor 414 itself in order to obtain a usable signal. In addition, the processor 414 may receive one or more signals from a wireless transceiver 524, a gestural control interface 328, a memory device 540, LEDS 544, or a short range transceiver 542, which may be used to communicate information from the processor 414 or communicate information to the processor 414 to be used to control, change or otherwise modify one or more functions of the earpiece 144, such as modality.

One or more sensors 416 may be operatively connected to the housing 152, the processor 414, and the analog-to-digital converter 522 and may sense one or more pieces of user data from the user or a third party. The sensors 416 may sense motion data, biological data, or environmental data which may be used to assist the earpiece 144 in determining whether data from an EEG electrode 418 should be used or is usable. For example, a MEMS gyroscope 332 installed within the earpiece 144 may produce one or more currents in response to one or more head movements from the user. This gyroscope current or signal could be used by the processor 414 to determine a head position, which may be used in conjunction with the EEG signal to ascertain a user gesture to control one or more functions of the earpiece 10. For example, gyroscope may send a signal indicative of a head nod, which is confirmed by the EEG signal and thus a phone call coming in on earpiece 144 could be answered based upon the head nod. Further, an electronic magnetometer 34 installed within the earpiece 10 may be used to measure the direction the user is facing through one or more voltages proportional to the strength and polarity of the Earth's magnetic field which may be used by the processor 414 in ascertaining a head movement relative to a fixed direction or to refine one or more measurements from other sensors 316. An electronic accelerometer 336 may produce a voltage in response to a user head movement may be used by the processor 414 to determine one or more accelerations related to the user and/or refine one or more EEG signals. And/or a bone conduction microphone 338 may measure sounds from the body and communicate them to the processor 414, which may be used to improve the signal quality of one or more EEG signals. However, the measurements taken by one or more of the aforementioned sensors 316 need not be related to the measurement of an EEG signal at all and can be used independently of the EEG signals as well.

One or more EEG electrodes 418 may be operatively connected to the housing 152, the processor 414 and the differential amplifier 20 and may be positioned anywhere on the surface of the earpiece 144 conducive for sensing an EEG signal from an ear surface. In at least one embodiment, at least one EEG electrode 418 should be positioned to receive an EEG signal from an outer ear surface and at least one EEG electrode 418 should be positioned to receive an EEG signal from an inner ear surface. One or more EEG electrodes 418 positioned on the outer ear surface may be used as a reference electrode in ascertaining an EEG signal, as more than one reading of an EEG signal should be obtained as the signal-to-noise ratio of an EEG signal is typically quite low. The EEG electrodes 418 will receive a current from the processor 414 in order to ascertain the impedances from a voltage drop associated with each EEG electrode 418 in order to determine which EEG electrodes 418 are good candidates to read an EEG signal from. EEG electrodes 418 having lower impedances obtain better quality signals than EEG electrodes 418 having higher impedances. EEG electrodes 418 having a sufficiently low impedance will receive an activation signal from the processor 414 to receive one or more EEG signals from the user. More than one EEG electrode 418 may receive the activation signal from the processor 414, and the activated EEG electrodes 418 may receive more than one EEG signal and may receive one or more EEG signals continuously or discretely. If the impedance of one of the activated EEG electrodes 418 becomes too high after receiving another activation signal from the processor 414 then processor 414 will stop using this electrode 418 for any further processing until the impedance drops below the predetermined acceptable level.

A differential amplifier 520 may be operatively connected to the housing 152, the processor 414, and each EEG electrode 418 and may be configured to improve the signal quality of each EEG signal received from the EEG electrodes 418. The differential amplifier 520 may remove any common mode noise present in the EEG signals received from the EEG electrodes and may also filter out noise received from outside electrical sources such as consumer electronic devices or appliances. For example, the differential amplifier 520 may remove common mode noise by subtracting the sum of all voltages received by the amplifier divided by the number of signals from each signal and subsequently amplifying the difference. The amplification may be anywhere from ten times to over ten thousand times, but too high an amplification may risk damaging one or more components of the earpiece 144. The differential amplifier 520 may remove other noise, such as noise received from consumer electronics in the 50-60 Hertz range and artifacts due to sweating or other user movement through one or more filters within the differential amplifier 520 itself. The filters may be passive high-pass filters, passive low-pass filters, quartz filters, or any other type of filter conducive to removing noise with frequencies.

An analog-to-digital converter 522 may be operatively connected to the housing 152, the processor 14, and the differential amplifier 520 and may receive EEG signals amplified and/or filtered by the differential amplifier 520, signals amplified and filtered from other components of the earpiece or signals directly from other parts of the earpiece 144. The analog-to-digital converter 522 may be an 8-bit, 12-bit, or higher bit converter, and may sample each signal it receives at a rate twice as high or more than the frequency of the signal in order to preserve the informational quality of the signal. The sampling frequency may be preset or inferred from the received signal. For example, the analog-to-digital converter 522 may receive an EEG signal with a higher than normal frequency due to amplification which may be higher than one-half the sampling rate, in which case the analog-to-digital converter 522 may readjust the sampling frequency upward in order to maintain the informational quality of the signal.

A wireless transceiver 524 may be operatively connected to the housing 152 and the processor 414 and may be configured to receive one or more signals from and transmit one or more signals to one or more external electronic devices. Any signals received by the wireless transceiver 524 may be transmitted to the processor 414 for further processing. The external electronic devices the wireless transceiver 524 may be configured to receive signals from include Bluetooth devices, mobile devices, desktops, laptops, tablets, modems, routers, communications towers, cameras, watches, third-party earpieces, earpieces, or other electronic devices capable of transmitting or receiving wireless signals. The signals received or communicated by the wireless transceiver 524 may encode for sound, instructions, or information which may be used in conjunction with the operation of the EEG electrodes 418. For example, a researcher performing tests on brain function may wish to have the EEG signals transmitted to a laptop or desktop computer for further study, or a user of the earpiece 144 may wish to download one or more applications related to using brain waves to control the earpiece 144. The wireless transceiver 524 may receive or transmit more than one signal simultaneously.

One or more microphones 160 may be operatively connected to the housing 152 and the processor 414 and may be configured to receive one or more voice commands which may be used to control one or more aspects of how the earpiece 144 handles one or more EEG signals. For example, the user may issue a voice command to cease receiving EEG signals, such as, "Stop receiving EEG signals" or something similar which is understood by the earpiece 144. In addition, the user may issue a voice command setting a sampling rate of the analog-to-digital converter 522 or how much a signal should be amplified to the differential amplifier 520. Other voice commands related to earpiece 144 functions but unrelated to EEG signal processing may be issued as well.

A gesture control interface 328 having at least one emitter 546 and a detector 548 may be operatively connected to the housing 152 and the processor 414 and may be configured to allow the user or a third party to control one or more functions of the earpiece 144. For example, a menu may be prompted through the use of a gesture with the gestural control interface 328, which may allow the user or a third party to set the sampling rate of the analog-to-digital converter 522, adjust the amplification ratio of any signals received by the differential amplifier 520, turn the earpiece on or off, or other functions unrelated to EEG signals such as listen to a song, playlist, newscast, podcast, or a weather report received through the wireless transceiver 524 or stored on the memory device 540, obtain information on the user's current surroundings, or anything else may be of interest to the user or a third party, and the aforementioned list is non-exclusive. The selections may be chosen through the use of one or more additional gestures or through the use of one or more voice commands from the user and/or a third party. The types of gestures may be used with the gesture control interface 328 to control the earpiece 144 include, without limitation, touching, tapping, swiping, use of an instrument, or any combination of the aforementioned gestures. Touching gestures used to control the earpiece 144 may be of any duration and may include the touching of areas not part of the gesture control interface 328. Tapping gestures used to control the earpiece 144 may include one or more taps and need not be brief. Swiping gestures used to control the earpiece 144 may include a single swipe, a swipe changes direction at least once, a swipe with a time delay, a plurality of swipes, or any combination of the aforementioned. An instrument used to control the earpiece 144 may be electronic, biochemical or mechanical, and may interface with the gesture control interface 328 either physically or electromagnetically.

A speaker 170 may be operatively connected the housing 152 and the processor 414 and may be configured to produce audio output derived from one or more signals from the wireless transceiver 524, the memory device 540, or the short range transceiver 542. The audio output conveyed by the speaker 170 may concern EEG functions or may relate to media or information the user desires to hear. Also, the speaker 170 may short out if the audio output exceeds a certain decibel level, which may be preset or programmed by the user or a third party.

A memory device 540 may be operatively connected to the housing 152 and the processor 414 and may be configured to store data, files, programs, or other information. The memory device 540 may store programs related to creating a measurement signal to measure an EEG electrode impedance, processing an EEG signal, amplifying an EEG signal, filtering an EEG signal, sampling an EEG signal, modifying an EEG signal, or programs unrelated to the reception and processing of an EEG signal. The memory device 540 may also contain programs related to storing information encoded in signals received by the wireless transceiver 524, transmitting files and/or communicating information via either the wireless transceiver 524 or the speaker 170 or instructions related to the operation of the earpiece 144. Information encoded in signals received by the wireless transceiver 524 may relate to algorithms for processing, amplifying, or filtering EEG signals or topics unrelated to EEG signal processing such as music, sounds, instrumentals, words, soundtracks, newscasts, podcasts, entertainment shows, commentary, advertisements, instructions, information, or anything else media or information related may be communicated by the speaker 170. Preloaded files may consist of programs required by the earpiece 144 to operate basic functions or troubleshoot one or more components of the earpiece 144 or another program.

A short range transceiver 542 may be disposed within the housing 152 and may be configured to receive signals from and to transmit signals to another transceiver disposed within another electronic device or even another earpiece. The short range transceiver 542 may receive or transmit more than one signal simultaneously. The short range transceiver 542 may be of any number of types including a near field magnetic induction (NFMI) transceiver as discussed in detail above.

One or more LEDs 544 may be operatively connected to the housing 152 and the processor 414 and may be configured to emit light in order to convey information to a user concerning the earpiece 144. The LEDs 544 may be located at any position on the earpiece 144 suitable for viewing by the user or a third party and may consist of as few as one diode which may be provided in combination with a light guide. In addition, the LEDs 544 may be discernable by a human eye or an electronic device and need not have a minimum luminescence.

An energy source 545 may be operatively connected to all of the components within the earpiece 144 and may be configured to store and release charge. The charge may come preinstalled with the earpiece 144, as may be the case with a battery, or the charge may derive from one or more signals from a wearable device, an external electronic device, such as smart case 102, or a combination of the aforementioned, as may be the case with a capacitor receiving one or more signals from a transceiver. The charge stored within the energy source 545 may be used to power one or more components of the earpiece 10. In addition, alternative battery-less power sources, such as thermal harvesting elements which create energy from a voltage generated by temperature differentials between a user's skin and the ambient environment (all of which are operatively connected to one or more earpiece 144), may be used to power the earpiece 144 as well.

FIG. 5 illustrates a flowchart of one embodiment of receiving an EEG signal from an ear surface using an earpiece 144. First, in step 602, a processor transmits a current to each EEG electrode 148. The current is a known quantity so an impedance may be calculated from the voltage drop across each EEG electrode 148.

In step 604, one or more sensors 416 receives at least one sensor reading. The sensor readings may be related to environmental data affecting EEG electrode readings or may be related to motion data picked up by a MEMS gyroscope 332, an electronic magnetometer 334, an electronic accelerometer 336 or a bone conduction microphone 338.

In step 606, the voltage drop associated with each EEG electrode 148 is communicated to the processor 414. The signal may be converted into a digital form by the analog-to-digital converter 522 before being sent to the processor 414.

In step 608, the sensor readings from at least one sensor 416 are communicated to the processor 414. The sensor readings may originate from an environmental sensor or a motion sensor such as a MEMS gyroscope 332, an electronic magnetometer 334 or an electronic accelerometer 336 and the sensor readings may be used by the processor 414 or differential amplifier 520 in removing artifacts present in one or more EEG signals.

In step 610, the processor determines an impedance associated with the voltage drop across each EEG electrode 418. The processor 414 may use an algorithm programmed within the processor or a memory device 540 operatively connected to the processor 414 to determine the impedances, and the processor 414 may perform the determination continuously or discretely as the situation arises.

In step 612, the processor 414 determines which impedances are below a programmed threshold. Lower impedances allow EEG electrodes to obtain EEG signals with better signal-to-noise ratios. The programmed threshold may be preprogrammed into the processor 414 or programmed by the user or a third party. The programming may be performed by the user or a third party using an external electronic device to transmit the instructions to the earpiece 144, through voice commands or gestures read by the earpiece, or the processor 414 may modify the threshold in response to one or more stimuli such as a sensor reading following instructions in an algorithm stored within the processor 414 or an external memory device operatively connected to the processor 414.

In step 614, the processor 414 creates an activation signal derived from the sensor readings and the impedances for each sensor 416, wherein the activation signal is only sent to EEG electrodes 418 which have an impedance below the programmed threshold. The processor 414 may use the sensor readings to modify which EEG signals receive the activation signal in order to reduce the level of noise in the received EEG signals and the processor 414 may create other signals as well which may or may not be related to the reception of an EEG signal.

In step 616, the processor 414 communicates the activation signal to each EEG electrode 418 which had an impedance below the programmed threshold. A few electrodes 418 may receive the activation signal even if none of the EEG electrodes have impedances below the programmed threshold. In this embodiment, the processor 414 communicates the activation signal to the two electrodes which have the smallest impedances.

In step 618, the activation signal activates the EEG electrodes 418 having impedances below the programmed threshold. Again, the activation signal may be sent to two or more EEG electrodes 418 if none of the electrodes 418 fall below the programmed threshold in order to obtain at least one EEG signal.

In step 620, the activated EEG electrodes 148 receive an EEG signal. At least two electrodes 148 are needed in order for the differential amplifier 520 to remove common mode noise (which should have different voltages) between the two signals.

As a further embodiment, after the EEG electrodes 148 receive one or more EEG signals, the signals, in step 622, are communicated to a differential amplifier 520 for amplification. At least two signals are required in order for the differential amplifier 520 to remove common mode gain, and additional signals may be used. The differential amplifier 520 may amplify the signal from ten to over ten thousand times depending on the voltage of the EEG signal after common mode noise removal or other requirements of the earpiece 144. In addition, one or more filters may be used to remove noise related to consumer electronics or artifacts related to sweating, body secretions, or body movement affecting the EEG signal.

In step 624, the amplified EEG signal is communicated to an analog-to-digital converter 522 for sampling. The sample rate of the analog-to-digital converter 522 should be at least twice the frequency of the amplified signal frequency in order to maintain the information content of the amplified signal, and the analog-to-digital converter may sample at 8-bits, 12-bits, 16-bits, or higher if desired.

In step 626, the sampled, amplified EEG signal (modified EEG signal) is communicated to the processor 414. The processor 414 may process the modified EEG signal using one or more algorithms stored within the processor 414 or a memory device 540 operatively connected to the processor 414 in order to determine a command, which may relate to controlling one or more functions of the earpiece 144. For example, the processor 414 may use a Fourier transform on an EEG signal to determine a command from a change in mu wave brain patterns from the user, such as turning the earpiece 144 on or off, selecting the next or last choice present in a listing communicated by the earpiece 144, or another function. The Fourier transform may break the EEG signals down into their frequency components, which are less affected by noise than the time domain EEG signals, making it easier for the processor to ascertain a command from a brain pattern.

The inventor(s) would like to reemphasize no longer would it be needed to place large and bulky electrodes on a user as is currently performed. The present invention provides for a distributed network of small electrodes 148 (FIG. 3) where the sum of the EEG signals could be summed to for a "virtual" large electrode. This distributed network of electrodes 148 overcomes the need for a trained expert to place the electrodes properly. An algorithm within processor 414 is capable of determining which combinations of electrodes 418 to use based upon the electrical impedance of each electrode 148 (discussed in great detail above). Further, the EEG signals from earpieces 142 and 144 can be compared, contrasted, summated or subtracted to form data input segments from both earpieces 142 and 144.

Figure 7:
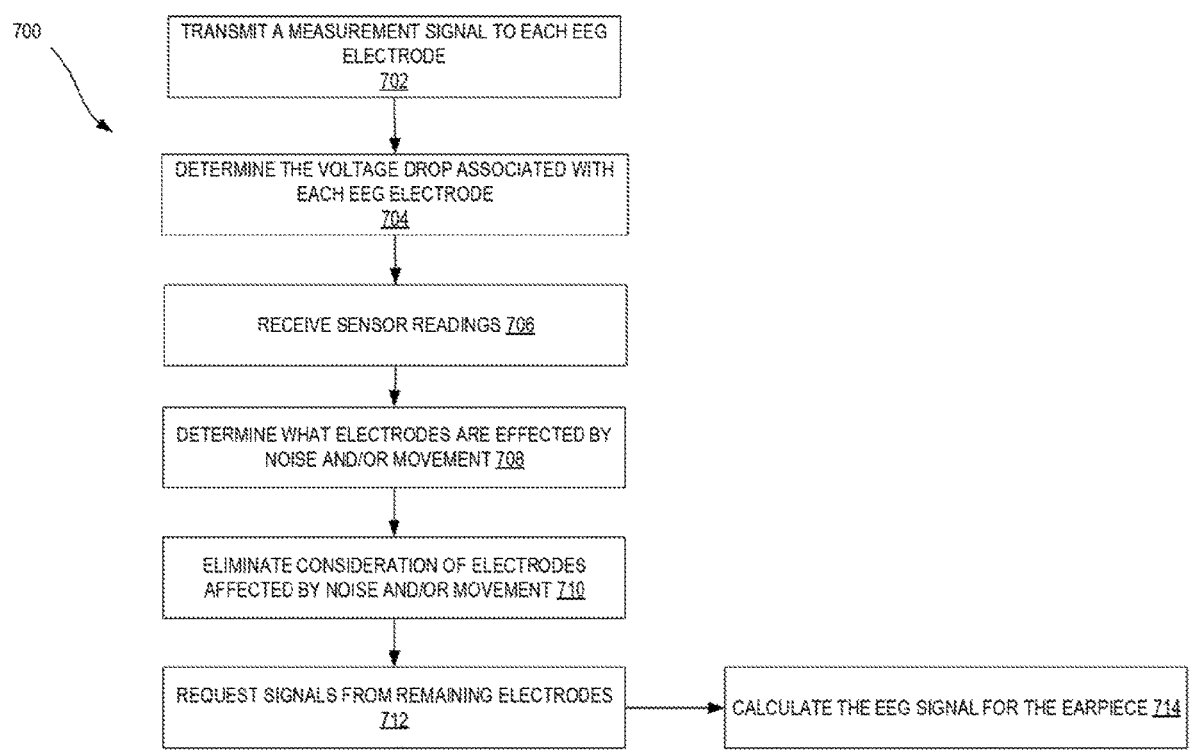
FIG. 7 is a block diagram for providing a large electrode in accordance with an illustrative embodiment.

With reference to FIGS. 3 and 7, an example and discussion of how to create a "virtual" large EEG electrode will be discussed. In FIG. 3 earpiece 144 is shown with 26 small EEG electrodes 148. In process 700, at step 702 a measurement voltage signal is sent to each EEG electrode 1 through 26. Processor 414 then calculates the voltage drop associate with each EEG electrode 148 at step 704. For purposes of this embodiment, we will say out of electrodes 1-26 only electrodes 1-9, 15-17 and 24-26 had an impedance below an accepted tolerance predetermined level (i.e., Z<predetermined threshold). Therefore, electrodes 148 10-14, 18-23 will be ignored and no signal will be requested from these electrodes 148. At step 706, processor 414 receives input from the sensors 416. Next, at step 708, processor 414 makes a determination as to what electrodes can still be used to collect data based upon potential signal noise caused by the environment or the user's movement. For purposes of the current example, we can propose the following:

Electrodes 1-9 were in an X-plane orientation
Electrodes 15-17 were in a Y-plane orientation; and
Electrodes 24-26 were in a Z-plane orientation.

This information, of course, could be provided by the magnetometer 334 (FIG. 5) discussed in great detail above. If processor 414 also has an input from accelerometer 336 which states at time T, there was motion in the X-plane, then processor 414 would then eliminate electrodes 1-9 from consideration for a representative EEG signal as the possibility for a noisy or bad signal would be too great (step 710). Other examples could include no pulsatile component from a heart rate sensor and no unusual magnetic field which may disqualify a EEG electrode as being sampled. Thus, at step 712, processor 414 would request a signal from electrodes 15-17 and 24-26. The EEG signals from electrodes 15-17 and 24-26 could then be pulled together by an algorithm on processor 414 to provide a compound EEG signal.

The invention is not to be limited to the particular embodiments described herein. In particular, the invention contemplates numerous variations in earpieces with in-ear electrodes. The foregoing description has been presented for purposes of illustration and description. It is not intended to be an exhaustive list or limit any of the invention to the precise forms disclosed. It is contemplated other alternatives or exemplary aspects are considered included in the invention. The description is merely examples of embodiments, processes or methods of the invention. It is understood any other modifications, substitutions, and/or additions can be made, which are within the intended spirit and scope of the invention.

What is claimed is:

1. A wireless earpiece for monitoring EEG data comprising:
   a housing;
   a processor disposed within the housing;
   a transceiver disposed within the housing and operatively connected to the processor;
   at least one sensor operatively connected to the processor; and
   a plurality of EEG electrodes operatively connected to the processor and positioned on the housing for receiving EEG signals from an ear surface;

wherein the processor measures an impedance of each of the plurality of EEG electrodes;
wherein the processor receives an EEG signal from each of the plurality of EEG electrodes;
wherein the processor processes the EEG signal from each of the plurality of EEG electrodes and creates a combined EEG signal;
wherein the combined EEG signal is shared with a second wireless earpiece via the transceiver.

2. The wireless earpiece for monitoring EEG data of claim 1, wherein a first EEG electrode of the plurality of electrodes is configured to be positioned to contact an outer surface of an ear and a second EEG electrode of the plurality of electrodes is configured to be positioned to contact an inner surface of an ear canal.

3. The wireless earpiece for monitoring EEG data of claim 1, wherein the processor will not accept any inputs from the plurality of EEG electrodes if their impedance is above a predetermined amount.

4. The wireless earpiece for monitoring EEG data of claim 3, wherein the processor accepts an input from the at least one sensor and refuses input from any of the plurality of EEG electrodes if the EEG data is compromised by noise detected by the at least one sensor.

5. The wireless earpiece for monitoring EEG data of claim 4, wherein the processor accepts inputs from the plurality of EEG electrodes, which have not been rejected due to impedance or sensor data and processes the EEG electrode inputs to create a reliable EEG signal.

6. A method of receiving an EEG signal from an ear surface comprising the steps of:
transmitting a current to a plurality of EEG electrodes;
receiving at least one sensor reading from a sensor operatively connected to a processor of an earpiece;
communicating, a voltage drop associated with of the plurality of EEG electrodes to the processor;
determining an impedance of each of the plurality of EEG electrodes;
determining which of the impedances are below a programmed threshold for each of the plurality of EEG electrodes;
transmitting an activation signal to the plurality of EEG electrodes which have an impedance below the programmed threshold;
receiving an EEG signal from each of the plurality of EEG electrodes which have an impedance below the programmed threshold;
processing the EEG signal from each of the plurality of EEG electrodes and creating a combined EEG signal by the processor;
transmitting the combined EEG signal by a transmitter of the earpiece to a second earpiece.

7. The method of claim 6, further comprising the step of determining which of the plurality of electrodes do not have a reliable EEG signal based upon the at least one sensor reading.

8. The method of claim 7, wherein the processor is housed within a wireless earpiece.

9. The method of claim 7, further comprising the step of providing a reliable EEG signal based upon the EEG signal taken from the plurality of EEG electrodes which have an impedance below the programmed threshold and have the reliable EEG signal based upon the at least one sensor reading.

10. A system comprising:
a first earpiece having a housing;
a processor disposed within the housing;
at least one sensor disposed within the housing and operatively connected to the processor, wherein the at least one sensor is configured to sense user data and communicate the user data to the processor; and
a plurality of EEG electrodes operatively connected to the processor and positioned on the housing for receiving EEG signals from an ear surface;
wherein the processor transmits a current to each of the plurality of EEG electrodes to determine an impedance from each of the plurality of EEG electrodes and subsequently communicates an activation signal to selected EEG electrodes if the impedance associated with the EEG electrode is below a programmed threshold;
wherein the processor communicates an activation signal to the selected EEG electrodes if the impedance associated with the EEG electrode is below a programmed threshold and the sensed user data does not indicate the electrode is unreliable;
wherein the selected EEG electrodes provide an EEG signal to the processor;
wherein the processor processes the EEG signal from the selected EEG electrodes and creates a combined EEG signal; and
wherein the combined EEG signal is shared with a second earpiece via a transmitter within the first earpiece.

11. The system of claim 10, wherein a modality of the first or the second earpiece is changed based upon the combined EEG signal.

12. The system of claim 11, wherein the modality of the first and second earpiece is changed based upon the combined EEG signal and the sensed user data.

* * * * *